(12) United States Patent
Tan et al.

(10) Patent No.: US 9,828,493 B2
(45) Date of Patent: Nov. 28, 2017

(54) CO-ATTRITED STABILIZER COMPOSITION HAVING SUPERIOR GEL STRENGTH

(71) Applicants: Zheng Tan, Princeton, NJ (US);
Michael Sestrick, Yardley, PA (US);
Nadia Yaranossian, Brussels (BE);
Jeremy Ondov, New York, NY (US)

(72) Inventors: Zheng Tan, Princeton, NJ (US);
Michael Sestrick, Yardley, PA (US);
Nadia Yaranossian, Brussels (BE);
Jeremy Ondov, New York, NY (US)

(73) Assignee: FMC Corporation, Philadelphia, PA (US)

( * ) Notice: Subject to any disclaimer, the term of this patent is extended or adjusted under 35 U.S.C. 154(b) by 393 days.

(21) Appl. No.: 14/362,652

(22) PCT Filed: Nov. 30, 2012

(86) PCT No.: PCT/US2012/067241
§ 371 (c)(1),
(2) Date: Jun. 4, 2014

(87) PCT Pub. No.: WO2013/085809
PCT Pub. Date: Jun. 13, 2013

(65) Prior Publication Data
US 2014/0364514 A1   Dec. 11, 2014

Related U.S. Application Data

(60) Provisional application No. 61/568,672, filed on Dec. 9, 2011.

(51) Int. Cl.

| | |
|---|---|
| *B01F 17/48* | (2006.01) |
| *B01F 17/00* | (2006.01) |
| *C08L 1/04* | (2006.01) |
| *A23C 9/154* | (2006.01) |
| *A23L 2/52* | (2006.01) |
| *A23C 11/10* | (2006.01) |
| *C08L 1/28* | (2006.01) |
| *A23L 2/66* | (2006.01) |
| *A01N 25/22* | (2006.01) |
| *A23L 2/62* | (2006.01) |
| *A61K 8/73* | (2006.01) |
| *A61K 47/36* | (2006.01) |
| *A61K 47/38* | (2006.01) |
| *A23L 29/262* | (2016.01) |
| *A61Q 11/00* | (2006.01) |
| *A61Q 19/00* | (2006.01) |

(52) U.S. Cl.
CPC ............ *C08L 1/04* (2013.01); *A01N 25/22* (2013.01); *A23C 9/1544* (2013.01); *A23C 11/103* (2013.01); *A23L 2/52* (2013.01); *A23L 2/62* (2013.01); *A23L 2/66* (2013.01); *A23L 29/262* (2016.08); *A61K 8/731* (2013.01); *A61K 8/732* (2013.01); *A61K 47/36* (2013.01); *A61K 47/38* (2013.01); *A61Q 11/00* (2013.01); *A61Q 19/00* (2013.01); *B01F 17/0092* (2013.01); *C08L 1/286* (2013.01); *A23V 2002/00* (2013.01); *A61K 2800/10* (2013.01); *A61K 2800/5922* (2013.01); *C08L 2205/02* (2013.01)

(58) Field of Classification Search
CPC combination set(s) only.
See application file for complete search history.

(56) References Cited

U.S. PATENT DOCUMENTS

| 2,978,446 A | 4/1961 | Battista et al. |
| 3,023,104 A | 2/1962 | Battista et al. |
| 3,145,146 A | 8/1964 | Lieberman et al. |
| 3,146,168 A | 8/1964 | Battista |
| 3,539,365 A | 11/1970 | Durand et al. |
| 3,573,058 A | 3/1971 | Tiemstra |

(Continued)

FOREIGN PATENT DOCUMENTS

| EP | 1226818 A1 | 7/2002 |
| EP | 1 681 048 A1 | 7/2006 |

(Continued)

OTHER PUBLICATIONS

Hawley's Condensed Chemical Dictionary, (2007), John Wiley & Sons, Inc. Online @ http://onlinelibrary.wiley.com/book/10.1002/9780470114735/titles headwords ="Avicel" [FMC], Algin, Cellulose-Microcrystalline, hydrocolloid, Starch, downloaded May 10, 2016), pp. 112, 36, 252, 664, 1174.*

(Continued)

Primary Examiner — Daniel S Metzmaier
(74) Attorney, Agent, or Firm — FMC Corporation

(57) ABSTRACT

The present invention is directed to a co-attrited stabilizer composition comprising: a) microcrystalline cellulose in an amount of from 20%-90% by weight of the composition; b) a hydrocolloid in an amount of from 5%-50% by weight of the composition, wherein the hydrocolloid is selected from at least one member of the group consisting of carboxymethyl cellulose having a degree of substitution of at least 0.95, pectin, alginate, carrageenan, xanthan gum, agar gum, wellan gum, or gellan gum; and c) a starch in an amount of from 5%-50% by weight of the composition, wherein the stabilizer composition has a gel strength (G') of at least 25 Pa when measured after 24 hours in a 2.6% solids water dispersion at 20° C. The composition is useful as a stabilizer, particularly in food and beverage products.

22 Claims, No Drawings

(56) References Cited

U.S. PATENT DOCUMENTS

| | | | |
|---|---|---|---|
| 3,639,169 A | 2/1972 | Broeg et al. | |
| 4,017,598 A | 4/1977 | Ohno et al. | |
| 4,110,476 A | 8/1978 | Rhodes | |
| 4,216,242 A * | 8/1980 | Braverman | A23G 9/32 |
| | | | 426/249 |
| 4,263,334 A | 4/1981 | McGinley | |
| 4,264,637 A | 4/1981 | Braverman | |
| 4,426,518 A | 1/1984 | Omiya | |
| 4,427,681 A * | 1/1984 | Munshi | A61K 9/0095 |
| | | | 516/105 |
| 4,693,750 A | 9/1987 | Bauer et al. | |
| 4,744,987 A | 5/1988 | Mehra et al. | |
| 4,980,193 A | 12/1990 | Tuason, Jr. et al. | |
| 5,082,684 A | 1/1992 | Fung | |
| 5,192,569 A | 3/1993 | McGinley et al. | |
| 5,209,942 A * | 5/1993 | Bauer | A23G 3/346 |
| | | | 426/573 |
| 5,272,137 A | 12/1993 | Blase et al. | |
| 5,286,510 A | 2/1994 | Bauer et al. | |
| 5,366,724 A | 11/1994 | Pierre et al. | |
| 5,366,742 A | 11/1994 | Tuason, Jr. et al. | |
| 5,409,907 A | 4/1995 | Blase et al. | |
| 5,415,804 A | 5/1995 | Minami et al. | |
| 5,505,982 A | 4/1996 | Krawczyk et al. | |
| 5,543,511 A | 8/1996 | Bergfeld et al. | |
| 5,573,777 A | 11/1996 | Serpelloni et al. | |
| 5,605,712 A | 2/1997 | Bertrand et al. | |
| 5,607,716 A | 3/1997 | Doherty et al. | |
| 5,609,898 A | 3/1997 | Kaji et al. | |
| 5,709,896 A | 1/1998 | Hartigan et al. | |
| 5,725,886 A | 3/1998 | Erkoboni et al. | |
| 5,747,067 A | 5/1998 | Auguello et al. | |
| 5,769,934 A | 6/1998 | Ha et al. | |
| 5,789,004 A | 8/1998 | Hogan et al. | |
| 5,866,166 A | 2/1999 | Staniforth et al. | |
| 6,010,734 A | 1/2000 | Whelan et al. | |
| 6,025,007 A | 2/2000 | Krawczyk | |
| 6,037,380 A | 3/2000 | Venables et al. | |
| 6,079,630 A | 6/2000 | Schroeder | |
| 6,106,865 A | 8/2000 | Staniforth et al. | |
| 6,117,474 A | 9/2000 | Kamada et al. | |
| 6,228,213 B1 | 5/2001 | Hanna et al. | |
| 6,235,947 B1 | 5/2001 | Yoshinari et al. | |
| 6,264,981 B1 | 7/2001 | Zhang et al. | |
| 6,270,830 B1 | 8/2001 | Kamada et al. | |
| 6,368,649 B1 | 4/2002 | van Bommel | |
| 6,372,782 B1 | 4/2002 | Patel et al. | |
| 6,391,368 B1 | 5/2002 | Tuason et al. | |
| 6,432,448 B1 | 8/2002 | Augello et al. | |
| 6,440,474 B1 | 8/2002 | Buliga et al. | |
| 6,475,539 B1 | 11/2002 | Dewille et al. | |
| 6,500,462 B1 | 12/2002 | Augello et al. | |
| 6,503,918 B2 | 1/2003 | Yoshinari et al. | |
| 6,517,871 B1 | 2/2003 | Venkatesh et al. | |
| 6,548,093 B1 | 4/2003 | Collinge et al. | |
| 6,689,405 B1 | 2/2004 | Tuason et al. | |
| 6,709,713 B2 | 3/2004 | Augello et al. | |
| 6,723,342 B1 | 4/2004 | Augello et al. | |
| 6,726,949 B2 | 4/2004 | Adolphi et al. | |
| 6,752,939 B2 | 6/2004 | Gereg | |
| 6,753,017 B2 | 6/2004 | Berkulin et al. | |
| 6,936,277 B2 | 8/2005 | Staniforth et al. | |
| 6,936,628 B2 | 8/2005 | Lee | |
| 7,462,232 B2 | 12/2008 | Tuason et al. | |
| 7,625,622 B2 | 12/2009 | Teckoe et al. | |
| 7,785,089 B2 | 8/2010 | Teckoe et al. | |
| 7,879,382 B2 | 2/2011 | Tuason et al. | |
| 8,927,609 B2 * | 1/2015 | Tan | C08L 1/04 |
| | | | 426/590 |
| 9,055,757 B2 * | 6/2015 | Tan | A23L 2/52 |
| 2003/0017204 A1 | 1/2003 | Tuason et al. | |
| 2003/0129238 A1 | 7/2003 | Augello et al. | |
| 2004/0071821 A1 | 4/2004 | Ashourian et al. | |
| 2004/0121006 A1 | 6/2004 | Kessel et al. | |
| 2004/0137043 A1 | 7/2004 | Augello et al. | |
| 2004/0185161 A1 | 9/2004 | Ashourian et al. | |
| 2004/0258827 A1 | 12/2004 | Shen | |
| 2005/0147710 A1 | 7/2005 | Teckoe et al. | |
| 2005/0220824 A1 | 10/2005 | Kessel et al. | |
| 2005/0233046 A1 | 10/2005 | Krawczyk et al. | |
| 2005/0233053 A1 | 10/2005 | Shen et al. | |
| 2005/0266116 A1 | 12/2005 | Teckoe et al. | |
| 2006/0096500 A1 * | 5/2006 | Tuason | A23C 9/137 |
| | | | 106/162.1 |
| 2006/0127451 A1 | 6/2006 | Augello et al. | |
| 2007/0128333 A1 * | 6/2007 | Tuason | A23C 9/1542 |
| | | | 426/615 |
| 2007/0264407 A1 | 11/2007 | Cerdena | |
| 2008/0131505 A1 | 6/2008 | Li et al. | |
| 2008/0131543 A1 | 6/2008 | Teckoe et al. | |
| 2008/0213360 A1 | 9/2008 | Thoorens et al. | |
| 2009/0110799 A1 | 4/2009 | Funami et al. | |
| 2009/0130287 A1 | 5/2009 | Tuason et al. | |
| 2011/0151097 A1 | 6/2011 | Tuason et al. | |
| 2011/0195163 A1 * | 8/2011 | Krawczyk | A21D 2/02 |
| | | | 426/321 |
| 2013/0064953 A1 * | 3/2013 | Bache | A23C 9/1544 |
| | | | 426/573 |
| 2013/0150462 A1 * | 6/2013 | Tan | C08L 1/04 |
| | | | 514/781 |
| 2014/0212563 A1 * | 7/2014 | Bache | A23L 1/0534 |
| | | | 426/573 |
| 2014/0370180 A1 * | 12/2014 | Tan | A23L 1/0534 |
| | | | 426/580 |

FOREIGN PATENT DOCUMENTS

| | | |
|---|---|---|
| GB | 1010477 | 11/1965 |
| GB | 1 567 049 | 5/1980 |
| GB | 2395413 A | 5/2004 |
| JP | 08-151481 A | 6/1996 |
| JP | 9266779 | 10/1997 |
| JP | 10-056960 | 3/1998 |
| JP | 10-237220 A | 9/1998 |
| JP | 11-046723 A | 2/1999 |
| JP | 11-299435 A | 11/1999 |
| JP | 2000-184853 | 7/2000 |
| JP | 2001-190220 A | 7/2001 |
| JP | 2002-125587 A | 5/2002 |
| JP | 2002345401 A2 | 12/2002 |
| JP | 2005-245217 | 9/2005 |
| SU | 467105 | 4/1975 |
| WO | WO 81-02521 A1 | 9/1981 |
| WO | WO 94/24888 A1 | 11/1994 |
| WO | WO 9502966 | 2/1995 |
| WO | WO 98/56826 A1 | 12/1998 |
| WO | WO 00/04862 A2 | 2/2000 |
| WO | WO 01/19348 A1 | 3/2001 |
| WO | WO 0132150 | 5/2001 |
| WO | WO 0132152 | 5/2001 |
| WO | WO 02/49451 A2 | 6/2002 |
| WO | WO 03/003843 A1 | 1/2003 |
| WO | WO 03/090558 A1 | 11/2003 |
| WO | WO 03/096976 A2 | 11/2003 |
| WO | WO 2005/030177 A2 | 4/2005 |
| WO | WO 2005/096832 A2 | 10/2005 |
| WO | WO 2006/131963 A1 | 12/2006 |
| WO | WO 2010136157 A1 | 12/2010 |
| WO | WO 2011/076572 A1 * | 6/2011 |

OTHER PUBLICATIONS

Hawley's Condensed Chemical Dictionary, (2007), John Wiley & Sons, Inc., headwords =Guar Gum 625, Hydrocolloid 664, (downloaded Aug. 27, 2016), Online @ http://onlinelibrary.wiley.com/book/10.1002/9780470114735/titles , pp. 1.*

AQUALON® Sodium Carboxymethylcellulose Physical and Chemical Properties Hercules, Hercules Incorporated 1999©, Wilmington, DE, USA, pp. 1-28.*

Mitchell, S.A., et al., 'A Compaction Process to enhance dissolution of poorly water-soluble drugs using hydroxypropyl methylcellulose'. International Journal of Pharmaceutics, 250, pp. 3-11, 2003.

(56) References Cited

OTHER PUBLICATIONS

Kleinebudde, P., 'Roll Compaction/Dry Granulation: Pharmaceutical Applications'. European Journal of Pharmaceutics and biopharmaceutics, 58, pp. 317-326, 2004.
DeyampertRogers, Tracey L., 'Content Considerations for Low Dosage Drug Formulations Processed by Roller Compaction'. Ph.D. Thesis, Purdue University, Aug. 1997.
Deyampert Rogers, Tracey L., 'Oral Preliminary Examination', Sep. 1, 1995.
Falzone, Angela Marie, 'Roller Compaction of Pharmaceutical Excipients and Excipient-drug Blends'. Ph.D. Thesis, Purdue University, Dec. 1990.
Skinner, G.W., 'The Evaluation of Fine-particle Hydroxyprpycellulose as a Roller Compaction binder in Pharmaceutical Applications'. Drug Development & Indust. Pharm, 25(10), pp. 1121-1128, 1999.
The Fitzpatrick Company Europe N.V., 'Introduction to Roll Compaction and the Fitzpatrick Chilsonator'. Mar. 1997.
Sheskey, P., et al. 'Roll Compaction Granulation of a Controlled-Release Matrix Tablet Formulation Containing HPMC'. Pharmaceutical Technology, Oct. 1999.
Zhang, Y., et al., 'Physical Properties and Compact Analysis of Commonly Used Direct Compression Binders'. AAPS Pharm. Sci. Tech. 4 (4) Article 62, Dec. 15, 2003.
Hsiu-o, H. et al., 'Characteristics of Codried Products of Microcrystalline Cellulose. with Saccharides and Low-substituted Hydroxypropylcellulose'. Powder Technology, 127 2002, pp. 45-53.
Gohel, M.C., 'A Review of Co-processed Directly Compressible Excipients'. Journal of Pharma, Pharma. Sci. 8(1), pp. 76-93, 2005.
Schroder, R. et al., 'Influcence of Magnesium Stearate on the Compaction Behavior and Tablet characteristics of Co-Spray Dried Compounds vs Physical Blends'. Poster Presented at American Association of Pharmaceutical Science (Denver) Oct. 2001.
Jacob, S. et al. 'Novel Co-processed Excipients of Mannitol and Microcrystalline Cellulose for Preparing Fast Dissolving Tablets of Glipzide'. Indian Journal of Pharmaceutical Sciences, vol. 69 (5) Sep.-Oct. 2007, pp. 633-639.
Rowe, Sheskey & Weller, "Handbook of PhannacueticaL Excipients, Fourth Edition", 2003, Pharmaceutical Press, London. XP002281910, p. 110, col. 2.
Sigma product info of carboxymethylcellulose, sodium salt (published Aug. 2003).
Bowman, B.J. Ofner, C.M.; Schott, H. "Colloidial Dispersions" Chapter 21 of Remington: The Science and Practice of Pharmacy, 21$^{st}$ Edition, 2005, Lippincott Williams and Wilkins, Philadelphia, PA.

* cited by examiner

US 9,828,493 B2

CO-ATTRITED STABILIZER COMPOSITION HAVING SUPERIOR GEL STRENGTH

FIELD OF THE INVENTION

The present invention relates to a co-attrited stabilizer composition that is suitable for use, for example, as a stabilizer for aqueous food and pharmaceutical systems, as well as to methods of making such a stabilizer composition and products containing such a stabilizer composition.

BACKGROUND OF THE INVENTION

Microcrystalline cellulose, also known and referred to herein as "MCC," hydrolyzed cellulose wet cake, or cellulose gel, is commonly used in the food industry to enhance the properties or attributes of a final food product. For example, it has been used as a binder and stabilizer in food applications, including in beverages, as a gelling agent, a thickener, a fat substitute, and/or non-caloric filler, and as a suspension stabilizer and/or texturizer. It has also been used as a binder and disintegrant in pharmaceutical tablets, as a suspending agent in liquid pharmaceutical formulations, and as a binder, disintegrant, and processing aid in industrial applications, in household products such as detergent and/or bleach tablets, in agricultural formulations, and in personal care products such as dentifrices and cosmetics.

Microcrystalline cellulose is modified for such uses by subjecting microcrystalline cellulose or "wet cake" to attriting processes to substantially subdivide the crystallites into finely divided particles. However, as particle size is reduced, the individual particles tend to agglomerate or hornify upon drying, a result that is undesirable in product manufacture or use. To prevent hornification, a protective colloid may be added during attrition or following attrition but before drying. The protective colloid wholly or partially neutralizes the hydrogen or other bonding forces between the smaller sized particles. The resulting materials are frequently referred to as attrited microcrystalline cellulose or colloidal microcrystalline cellulose and such attrited or colloidal microcrystalline cellulose will typically form stable suspensions with little to no settling. In contrast, non-colloidal microcrystalline cellulose will settle and not form a stable suspension in aqueous systems. Colloidal microcrystalline cellulose, such as carboxymethyl cellulose-coated microcrystalline cellulose, is described in U.S. Pat. No. 3,539,365 (Durand et al.). Another colloidal microcrystalline cellulose, such as starch-coated microcrystalline cellulose, is described in US Pat. App. 2011/0151097 (Tuason et al.). FMC Corporation (Philadelphia, Pa., USA) manufactures and sells various colloidal microcrystalline cellulose products, including edible food and pharmaceutical grades, under the names of, among others, AVICEL® and GELSTAR®.

Admixtures of MCC and some hydrocolloids (such as carboxymethyl cellulose having a degree of substitution of at least 0.95, pectin, alginate, carrageenan, xanthan gum, agar gum, wellan gum, or gellan gum) may be too 'slippery' to be satisfactorily attrited. Less than satisfactory attrition of the MCC particles can have a deleterious effect on the functionality of the MCC stabilizer. As a result, some attempts have been made to solve this problem by using an attriting agent, for instance, a salt. For example, see U.S. Pat. No. 7,879,382, U.S. Pat. No. 7,462,232 and U.S. Pat. No. 5,366,724. Other approaches have been taken to make suitable MCC/hydrocolloid compositions. For example, see US 2005/0233046; US 2011/0151097; and WO 2010/136157.

There remains a need, however, for a co-attrited colloidal microcrystalline cellulose composition containing the hydrocolloids of the present invention wherein the composition has a gel strength previously unobtainable. Applicants have unexpectedly found that co-attriting MCC and the hydrocolloids of the present invention with starch produces a stabilizer composition that has unexpected gel strength in aqueous systems. Such a stabilizer composition provides significant commercial and industrial advantages.

SUMMARY OF THE INVENTION

The present invention is directed to a co-attrited stabilizer composition comprising: a) microcrystalline cellulose in an amount of from 20%-90% by weight of the composition; b) a hydrocolloid in an amount of from 5%-50% by weight of the composition, wherein the hydrocolloid is selected from at least one member of the group consisting of carboxymethyl cellulose having a degree of substitution of at least 0.95, pectin, alginate, carrageenan, xanthan gum, agar gum, wellan gum, or gellan gum; and c) a starch in an amount of from 5%-50% by weight of the composition, wherein the stabilizer composition has a gel strength (G') of at least 25 Pa when measured after 24 hours in a 2.6% solids water dispersion at 20° C.

The present invention is also directed to a method for making the stabilizer composition comprising: a) admixing the microcrystalline cellulose, hydrocolloid of the present invention, and starch, wherein the microcrystalline cellulose is present in an amount of 20%-90% by weight of the composition, the hydrocolloid of the invention is present in an amount of 5%-50% by weight of the composition, and the starch is present in an amount of 5%-50% by weight of the composition; b) co-attriting the admixture of step a); and c) drying the extrudent of step b).

The present invention is also directed to various products containing such a stabilizer composition.

DETAILED DESCRIPTION OF THE INVENTION

The present invention encompasses microcrystalline cellulose compositions made by co-attriting a) microcrystalline cellulose, b) a hydrocolloid selected from at least one member of the group consisting of carboxymethyl cellulose having a degree of substitution of at least 0.95, pectin, alginate, carrageenan, xanthan gum, agar gum, wellan gum, or gellan gum, and c) a starch. The presently claimed stabilizer may be obtained with or without using a salt attriting agent in the co-attrition step. The resulting material is colloidal and characterized by a having a range of gel strength previously unobtainable.

Particular embodiments include, but are not limited to, co-attrited three-component compositions of (i) MCC, carboxymethyl cellulose having a degree of substitution of at least 0.95, and starch; (ii) MCC, pectin and starch; (iii) MCC, carrageenan and starch; (iv) MCC, alginate, and starch; (v) MCC, xanthan and starch; (vi) MCC, agar gum and starch; and (vii) MCC, wellan gum and/or gellan gum and starch. The resulting products are useful as stabilizers in various applications, including edible food products. In other embodiments, the resulting stabilizer compositions are adapted for use in pharmaceutical products, nutraceutical products, healthcare products, cosmetic products, personal care products, consumer products, agricultural products, or chemical formulations.

In particular, the present invention provides compositions that generally include negatively charged hydrocolloids (carboxymethyl cellulose having a degree of substitution of at least 0.95, pectin, alginate, carrageenan, xanthan gum, agar gum, wellan gum, or gellan gum) that are 'slippery' when combined with MCC. In the context of this disclosure, "slippery" or "slipperiness" refers to a physical characteristic of MCC and the hydrocolloid of the present invention that makes it difficult to create a sufficient level of attrition to produce the desired stabilizer.

"Colloid" and "colloidal" are used interchangeably in the present specification to define particles that are capable of being properly suspended in an aqueous mixture. As known to those of ordinary skill in the art and referred to herein, colloidal particles may be of any suitable particle size, provided that they are able to form uniform suspensions; e.g., when measured in suspension, a majority of the particles may have a particle size of from 0.1 to 30 microns.

As used herein, the terms "attrited" and "attrition" are used interchangeably to mean a process that effectively reduces the size of at least some if not all of the particles to a colloidal size. "Co-attrition" is a term used to refer to the application of shear forces to an admixture of components. Suitable attrition processes may be accomplished, for example, by co-extruding, milling, admixing, or kneading.

"Gel strength (G')" refers to the reversibly stored energy of the system (the elastic modulus G') and relative to the compositions herein is a function of the cellulose concentration. The measurement is made using a TA-Instruments rheometer (ARES-RFS3) with oscillatory strain sweep at 1 Hz and at 20° C., with gap size at 1.8 mm in a 2.6% solids water (de-ionized) dispersion after 24 hours.

Further, edible food products are disclosed that contain the present compositions. These food products may include aqueous systems, emulsions, beverages, sauces, soups, dressings, dairy and non-dairy milks and products, frozen desserts, and cultured foods. The edible food products can additionally comprise diverse edible material and additives, including proteins, fruit juices, vegetable juices, fruit-flavored substances, or any combination thereof. In addition, a number of industrial suspensions are disclosed that comprise the present compositions that are adapted for use in pharmaceutical products, cosmetic products, personal care products, agriculture products, or chemical formulations.

Microcrystalline Cellulose

Any MCC may be employed in compositions of the present invention. MCC from any source may be employed in the compositions of the present invention. Feedstocks from which MCC may be obtained include, for example, wood pulp (such as bleached sulfite and sulfate pulps), corn husks, bagasse, straw, cotton, cotton linters, flax, hemp, ramie, seaweed cellulose, and fermented cellulose. Additional feedstocks include bleached softwood kraft pulps, bleached hardwood kraft pulps, bleached Eucalyptus kraft pulps, paper pulps, fluff pulps, dissolving pulps, and bleached non-wood cellulosic pulps. In one embodiment, the MCC used is one approved for human consumption by the United States Food and Drug Administration.

The microcrystalline cellulose may be in any suitable form. The microcrystalline cellulose used in the co-attrition step is preferably in the form of a "wet cake." A microcrystalline cellulose wet cake is a microcrystalline cellulose that has been manufactured in a wet form (e.g., containing water) and has not been dried ("never dried"). In other words, a microcrystalline cellulose wet cake is microcrystalline cellulose that has not been previously dried and re-hydrated with water. Microcrystalline cellulose (MCC) may comprise tiny rodlike microcrystals of partially hydrolyzed cellulose (beta-1,4 glucan). The beta-1,4 glucan may be derived from any desired chemical degradation method applied to a selected cellulose material.

Microcrystalline cellulose is produced by treating a source of cellulose, preferably alpha cellulose in the form of pulp from fibrous plant materials, with a mineral acid, preferably hydrochloric acid (acid hydrolysis). The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 60 percent moisture, is referred to in the art by several names, including 'hydrolyzed cellulose', 'hydrolyzed cellulose wet cake', 'level-off DP cellulose', 'microcrystalline cellulose wet cake', or simply 'wet cake'.

The classic process for MCC production is acid hydrolysis of purified cellulose, pioneered by O. A. Battista (U.S. Pat. Nos. 2,978,446; 3,023,104; and 3,146,168). Various chemical or mechanical treatments may be used to enhance the MCC acid hydrolysis. In efforts to reduce the cost while maintaining or improving the quality of MCC, various alternative processes have also been proposed. Among these are steam explosion (U.S. Pat. No. 5,769,934; Ha et al.), reactive extrusion (U.S. Pat. No. 6,228,213; Hanna et al.), one-step hydrolysis and bleaching (World Patent Publication WO 01/0244; Schaible et al.), and partial hydrolysis of a semi-crystalline cellulose and water reaction liquor in a reactor pressurized with oxygen and/or carbon dioxide gas and operating at 100° C. to 200° C. (U.S. Pat. No. 5,543,511).

The MCC is typically present in the stabilizer composition of the invention in an amount of from 20-90% by weight, more specifically, 40-75% by weight, 45-70% by weight, and 50-70% by weight of the co-attrited stabilizer composition. All % by weights provided in this paragraph are on a dry basis and, for example, exclude water.

Starch

The starch may be any suitable starch (e.g., native starch, or starch derivative known to one skilled in the art) or combination of starches and may come from any source (e.g., wheat, corn, oat, rice, tapioca, potato, etc. or a mixture thereof). While the starch may have any suitable amylose content, in a particular embodiment, the starch may have a low amylose content because amylose has the tendency to retrograde (i.e., can come together and form some bonds that will force out the water). As a result, the starch may lose its water absorbing properties.

The starch that may be used in the present invention includes any chemically, physically, or genetically modified forms of starch. For example, the at least one starch may be selected from the group consisting of hydroxyalkyl starch, hydroxyethylated starch, hydroxypropylated starch, acyl starch, and mixtures thereof. In a particular embodiment, the chemically modified starches are derived from hydroxyalkyl substituted starches, with low to medium cross-links (or no cross-links), such as by phosphates or other common chemical cross-linking means. In one embodiment, the at least one starch comprises tapioca starch, corn starch, derivatives thereof, and mixtures thereof.

In an exemplary embodiment, the starch comprises a high amylopectin starch, such as tapioca (also known as Cassava or Manioc). In one embodiment, the starch includes or is a tapioca-based starch. The tapioca-based starch may be unmodified tapioca (e.g., native tapioca starch) or a tapioca derivative. In a particular embodiment, the starch is a tapioca derivative, such as a modified tapioca starch comprising a hydroxypropyl diphosphate tapioca starch, a hydroxypropyl tapioca starch, or mixtures thereof, for example.

The starch may be a hydroxyalkyl starch, such as a $C_2$-$C_5$ hydroxyalkyl starch. The hydroxyalkylation of a native starch can be brought about by reacting a native starch with alkylene oxides with the appropriate number of carbon atoms. Without wishing to be bound to a particular theory, it is believed that the formation of a hydroxyl group, which is bound to the starch backbone via an alkyl group with 2 to 5 carbon atoms, may lead to a desired hydrophilic-lipophilic balance of the starch. The position of the hydroxyl group on the alkyl group is not critical. The average degree of substitution, the average number of substituted OH groups of the starch molecule per anhydroglucose unit, of the hydroxyalkylation is preferably approximately 0.08 to 0.3. Particularly preferred starches are hydroxyethylated and/or hydroxypropylated starches obtained by reacting starches with ethylene oxide or propylene oxide, respectively. A starch to be used according to the invention can also contain more than one hydroxyl group per alkyl group. Hydroxypropylation of starches (degree of substitution determines the number of functional groups) may provide certain useful properties, such as freeze-thaw stability, eliminate retrogradation issues, etc., in various food systems.

The starch may also be an acyl starch, such as a $C_2$-$C_{18}$ acyl starch. Acylation generally takes place by reaction with acid anhydrides of general formula $(R—C(O))_2O$, in which R is an alkyl group, such as methyl or ethyl; suitable acid anhydrides include, but are not limited to, succinic and maleic anhydride and their alkylated derivatives. $C_2$-$C_{18}$ acyl starch may be brought about by crosslinking with $C_2$-$C_{18}$ alkanoate or alkenoate and may be additionally acylated for a suitable hydrophilic-lipophilic balance with an average degree of substitution of 0 to 0.8, particularly 0 to 0.5.

In a preferred embodiment, the starch may be a chemically modified, cross-linked starch. A preferred crosslinking method is phosphorylation, in which the starch (such as a hydroxyalkylated starch) is reacted with phosphorous oxychloride, phosphorous pentoxide, and/or sodium trimetaphosphate. Two starch chains are crosslinked by an anionic P—O group. Another preferred crosslinking method is by using $C_4$-$C_{18}$ alkane or alkene dicarboxylic acids, preferably $C_4$-$C_8$ alkane dicarboxylic acids, and in particular, adipic acid. The alkane or alkene dicarboxylic acid links two starch chains via ester bonds. It may be in straight or branched chain form. The derivatives may be obtained, e.g., by reacting the starch with the mixed anhydrides of dicarboxylic acid and acetic acid. Based on the dry starch, in general, less than 0.1 wt. %, typically about 0.06 wt. %, of crosslinking agent is used.

The starches may either be non-gelatinized or pre-gelatinized.

In low pH applications, the starch is preferably a food-grade modified low pH stable starch. As the name implies, the starch is "food-grade" because it is deemed suitable for human consumption, the starch is "modified" as in chemically modified and/or cross-linked, and is "low pH stable" meaning it is stable in acidic conditions. In an embodiment of the present invention, the starch derivative is selected from the group consisting of a hydroxypropyl di-starch phosphate, an acetylated di-starch adipate, and a sodium hydroxypropyl starch phosphate. In a preferred embodiment, the food-grade modified low pH stable starch is a modified tapioca starch, a modified corn starch, and mixtures thereof. The modified tapioca starch may include, for example, a hydroxypropyl diphosphate tapioca starch, a hydroxypropyl tapioca starch, and mixtures thereof.

In a preferred embodiment, the food-grade modified low pH stable starch is hydroxypropyl distarch phosphate, which is a low pH crosslinked hydroxypropylated starch (containing, for example, 24% amylose and 76% amylopectin). A suitable hydroxypropyl distarch phosphate starch is available, for example, as PURE GEL™ B-994 from Grain Processing Corporation with headquarters in Muscatine, Iowa. Without wishing to be bound to a particular theory, crosslinking with phosphoryl oxychloride at a high pH (for example, pH 11) may produce a distarch phosphate that is heat, shear, and acid stable. In other words, the starch granules remain intact and are not ruptured under high shear conditions and maintain their water absorbing properties under low pH conditions. Accordingly, a greater crosslinking may be desirable for certain low pH food applications because the starch is more acid stable with more crosslinking.

In some food applications, it may be preferable that unmodified starch (without chemical modification) is used. In other applications, the starch used can be physically modified, yet still be classified or labeled as "starch". Such examples include the Novation series starches from National Starch Company.

In some embodiments, high amylose starch, microcrystalline starch or resistant starches may be used. In such cases, these starches may be mixed with other starches or modified starches.

The at least one starch is generally present in an amount of 5-50% by weight of the co-attrited stabilizer composition, more specifically, 10-50% by weight, 20-50% by weight, 10-40% by weight, 15-40% by weight, 15-35% by weight, and 15-30% by weight of the co-attrited stabilizer composition. All % by weights provided in this paragraph are on a dry basis.

Since MCC wet cake is slightly negatively charged, the group of negatively charged hydrocolloids of the present invention (discussed below) form slippery complexes with MCC. As discussed above, a 'slippery' hydrocolloid presents processing challenges that make it difficult to obtain the sufficient level of attrition necessary for making a MCC stabilizer composition. The inventors have unexpectedly found that attriting MCC and hydrocolloids of the present invention with starch produces an MCC stabilizer composition having unexpectedly superior gel strength (G').

Hydrocolloids

The hydrocolloids used in the present invention are negatively charged hydrocolloids. These hydrocolloids are slippery, e.g., when co-attrited with MCC and comprise carboxymethyl cellulose having a degree of substitution ("DS") of at least 0.95, pectin, alginate, carrageenan, xanthan gum, agar gum, wellan gum, or gellan gum and mixtures thereof. These specific hydrocolloids are sometimes referred to herein as "negatively charged hydrocolloids."

One example of the hydrocolloid of the present invention is carboxymethyl cellulose (sometimes referred to herein as "CMC") having a DS of at least 0.95. Such a carboxymethyl cellulose can be an alkali metal carboxymethyl cellulose, more particularly sodium, potassium, or ammonium carboxymethyl cellulose, and most preferably sodium carboxymethyl cellulose.

Carboxymethyl cellulose is characterized by, inter alia, the DS. The DS represents the average number of hydroxyl groups substituted per anhydroglucose unit. For example, each anhydroglucose unit in carboxymethyl cellulose contains three hydroxyl groups, which gives carboxymethyl cellulose a maximum theoretical DS of 3.0. The carboxymethyl celluloses contemplated for use in the present methods have a DS of at least 0.95. In some embodiments, the carboxymethyl cellulose has a DS of 0.95 to 1.5. In still other embodiments, the carboxymethyl cellulose has a DS of about 0.95 to 1.2. In a yet further embodiment, the carboxymethyl cellulose has a DS of 1.15-1.5. Preferably, carboxymethyl cellulose having a DS of 0.95-1.5 is used in embodiments of the present three-component invention. A carboxymethyl cellulose having a DS less than, for example, 0.85 is generally less negatively charged, and is less "slippery" when extruded with MCC.

The carboxymethyl cellulose is also characterized by, inter alia, viscosity, when measured, for example, at 2% solids in water at 25° C. (using a Brookfield viscometer and appropriate spindle and speed). "Low viscosity" carboxymethyl cellulose has a range of about 10 to 200 cps, more particularly, a viscosity of 10-100 cps, more particularly, a viscosity of 30-60 cps (e.g., when measured using a Brookfield viscometer at 2% solids in water, 25° C., at 60 rpm, spindle #1). "Medium viscosity" carboxymethyl cellulose has a range of about 200 to 4,000 cps (e.g., when measured using a Brookfield viscometer at 2% solids in water, 25° C., at 30 rpm, spindle #2). A particular "medium viscosity" carboxymethyl cellulose has a range of about 200-3000 cps, and a more particular "medium viscosity" carboxymethyl cellulose has a range of about 300-900 cps. Any carboxymethyl cellulose that has higher viscosity than "medium viscosity" may be considered "high viscosity" grade carboxymethyl cellulose (and such viscosity can be measured using a Brookfield viscometer at 2% solids in water, 25° C., at 30 rpm, spindle #3 or #4). In the present invention of co-attrited three component admixture, carboxymethyl cellulose of any viscosity may be used.

Commercially available carboxymethyl celluloses having a DS of at least 0.95 include Ambergum 1221 (Ashland; a low viscosity carboxymethyl cellulose having a DS of about 1.2), 12M8F (Ashland; a medium viscosity carboxymethyl cellulose having a DS of about 1.2) and 12M31P (Ashland: a medium viscosity carboxymethyl cellulose having a DS of about 1.2).

Additional hydrocolloids useful in the present invention include carrageenans (iota, lambda, kappa, kappa-2, mu, nu, theta, or mixtures thereof), alginate, pectins (including high methoxyl ("HM"), low methoxyl pectins, and acetylated pectins (such as beet pectin)), xanthan gums, agar gums, wellan gums, gellan gums and mixtures thereof. Semi-refined carrageenans are also useful in the present invention (these are less purified forms of the carrageenans that may contain some of the structural components of the seaweed such as cellulose). A preferred alginate is sodium alginate.

The hydrocolloid used in the present invention is typically present in an amount of 5-50% by weight, more particularly, 5-30%, 5-20% by weight, 5-15% by weight, 10-30% by weight, and 10-20% by weight of the stabilizer composition. All % by weights provided in this paragraph are on a dry basis.

The co-attrited stabilizer composition of the present invention may or may not contain a co-attriting agent such as a salt.

Co-Attrition

Methods for forming the colloidal compositions are provided herein. The MCC (e.g., wet cake), starch, and negatively charged hydrocolloid components are intimately associated with one another during co-attrition to achieve sufficient interaction among the components. An attriting salt solution may or may not be used. It has unexpectedly been discovered that the three-component composition of the present invention is not slippery, generates very good work profile, and upon dispersion yields gel strengths previously unobtainable.

The gel strength (G') of the co-attrited stabilizer composition is very high; i.e., at least 25 Pa, at least 42 Pa, at least 45 Pa, at least 50 Pa and at least 55 Pa, when measured after 24 hours in a 2.6% solids water dispersion at 20° C. The gel strength (G') may be as high as 200 Pa, 250 Pa or 300 Pa.

Preferably, the MCC wet cake has a solids level of between 35%-70% (more preferably, 35%-60% solids), while the negatively charged hydrocolloid and the starch are added into the wet cake as dry powders. The methods include mixing the negatively charged hydrocolloid (5-50% weight) with MCC (20-90% weight) and with the starch (5-50% weight). A co-attriting salt may or may not be used as an attriting agent. A particular weight ratio of the three components is about 10-30% negatively charged hydrocolloid, 40-75% MCC, and 20-50% starch. In one embodiment, the particular weight ratio is 10-20% negatively charged hydrocolloid, 40-70% MCC, and 20-40% starch.

The co-attrition causes the starch and negatively charged hydrocolloid to at least partially, if not fully, surround the microcrystalline cellulose particles. In other words, the starch and negatively charged hydrocolloid act as a barrier dispersant for the microcrystalline cellulose wet cake so that the particles of microcrystalline cellulose do not aggregate together.

Without being bound by any theory, it is believed that during the co-attrition of the admixture of MCC/negatively charged hydrocolloid/starch, the starch unexpectedly intermingles with the negatively charged hydrocolloid in a way that significantly reduces the slipperiness of the admixture and also contributes constructively to the gel development of a final product containing the admixture. This results in more intimate interactions between MCC crystallites. It is also hypothesized that starch with higher amylopectin (from sources such as tapioca, corn, rice, etc.) and modified starches (such as alkylated starches) are particularly effective in developing this unexpected level of gel structure.

According to one embodiment of the present invention, a composition for use in a food application (such as ice cream, cooking cream, etc.) comprises a co-attrited admixture of microcrystalline cellulose wet cake, at least one tapioca starch or starch derivative, and a carboxymethyl cellulose having a DS of at least 0.95, wherein the resulting colloidal microcrystalline cellulose is at least partially coated by the at least one tapioca starch or starch derivative or the carboxymethyl cellulose.

In another embodiment of the present invention, a water-dispersible composition for use in a food application comprises a co-attrited admixture of microcrystalline cellulose wet cake, starch, and the negatively charged hydrocolloid, wherein the resulting colloidal microcrystalline cellulose is at least partially coated by a barrier dispersant comprising the negatively charged hydrocolloid and starch. One of the intended applications of this composition is an acid stable formulation for low pH food applications.

In a preferred embodiment, the MCC, starch, and negatively charged hydrocolloid are co-attrited using medium or high shear conditions to minimize the microcrystalline cellulose aggregates and to form the coating of starch and negatively charged hydrocolloid on the surface of the microcrystalline cellulose. Suitable medium to high shear conditions may be obtained, for example, by co-extruding the MCC wet cake, starch, and negatively charged hydrocolloid in an extruder.

The water in the MCC wet cake or any additional water present in the final admixture may be present in less than 75% water by weight. In one embodiment, the water content during co-attriting is in an amount of about 20-70% water by weight of the admixture, more preferably, about 25-50% water. Thus, the admixture preferably comprises some water (e.g., in the wet cake), but not too much.

As discussed above, the MCC used during the co-attrition step is typically in wet cake form, but can be used in dried or re-hydrated form. While the starch or negatively charged hydrocolloid (preferably in dry powder form) may be allowed to hydrate to some degree by interacting with the water in the MCC wet cake, it is preferred to keep the amount of water present in the admixture to a minimum (so as to ensure sufficient levels of attrition are able to be achieved). The use of MCC wet cake is preferred and does not need to be diluted with water (and is preferably not diluted with water).

In an embodiment of the present invention, the co-attrited admixture of microcrystalline cellulose, starch, and negatively charged hydrocolloid is dried. The drying may be carried out by a variety of means, such as by spray drying, oven drying, freeze drying, drum drying, flash drying, fluidized bed, vacuum drying, bulk drying, or thermal reactor drying. The drying removes water from the composition to obtain a product that would be recognized by one skilled in the art as a "dried" product. The dried water-dispersible composition comprises the co-attrited admixture of colloidal microcrystalline cellulose, starch, and negatively charged hydrocolloid.

For spray drying, the extrudent is dispersed in water to form a slurry, optionally homogenized, and then spray dried. Dry particles formed from the spray drying can be reconstituted in a desired aqueous medium or solution to form the compositions, edible food products, and industrial application suspensions described herein.

Formulations Using the Stabilizer Composition

The co-attrited stabilizer compositions of the present invention can act as stabilizers in a variety of industrial and consumer uses. In particular, these applications include food (e.g., beverage), pharmaceutical, health care, agrochemical and other industrial applications.

The stabilizer compositions, after drying to powder form, can be mixed with an aqueous solution to form a stable colloidal suspension. In some embodiments, the stabilizer compositions maintain their colloidal properties for greater periods of time and under more harsh conditions than previously known compositions. The edible food products formed using the stabilizer compositions described herein are capable of providing stable colloidal properties for extended periods even at acidic pH conditions.

Some examples of the edible food products include the following: suspensions, sauces (especially low pH/high salt types), retorted soups, dressings (including both spoonable and pourable dressings), beverages (including those that are heat treated, for example, by pasteurization or ultra pasteurization, or heat treated using ultra high temperature (UHT) or high temperature short time (HTST) or retort processes, UHT and retort processed protein and nutritional beverages, UHT processed low pH protein-based beverages, UHT Calcium fortified beverages, UHT milk-based beverages), UHT and retort processed milk creams, low pH frozen desserts (e.g., fruit sherbets), aerated food systems, dairy and non-dairy based, cultured products (sour cream, yogurts), and bakery fillings or creams. More specific examples of beverages containing the stabilizer composition of the invention include dairy beverages, e.g., dairy beverages containing milk (including low and no fat milk) and flavored milks such as chocolate milk.

The use levels of the stabilizer compositions in food products can range from about 0.05% to about 3.5% by weight of total food product, and in some instances can be 0.2% to 2% by weight of total food product. In some of these edible food products, an adjunct stabilizer (that is not part of the co-attrited stabilizer) can be added to the food product to further assist in increasing long term stability (e.g., additional carboxymethyl cellulose or hydrocolloid can be added in the amounts of about 0.05% to about 0.5% of the food product).

The food products can also include other edible ingredients such as, for example, vegetable or fruit pulps, mineral salts, protein sources, fruit juices, acidulants, sweeteners, buffering agents, pH modifiers, stabilizing salts, or a combination thereof. Those skilled in the art will recognize that any number of other edible components may also be added, for example, additional flavorings, colorings, preservatives, pH buffers, nutritional supplements, process aids, and the like. The additional edible ingredients can be soluble or insoluble, and, if insoluble, can be suspended in the food product.

Some of the edible food products that may contain the stabilizer composition of the invention may comprise protein and/or fruit juice (e.g., fruit juices containing solids (such as pulp) and nectars are readily stabilized by adding the stabilizer compositions). In such blends having only juice or only protein, the composition of the stabilizer composition and the amount of stabilizer composition used in the beverage blend may need to be adjusted accordingly to maintain the desired stability results. Such routine adjustment of the composition is fully within the capabilities of one having skill in the art and is within the scope and intent of the present invention. These edible food products can be dry mix products (instant sauces, gravies, soups, instant cocoa drinks, etc.), low pH dairy systems (sour cream/yogurt, yogurt drinks, stabilized frozen yogurt, etc.), baked goods, and a bulking agent in non-aqueous food systems and in low moisture food systems.

Suitable juices incorporating the stabilizer composition include fruit juices (including but not limited to lemon juice, lime juice, and orange juice, including variations such as lemonade, limeade, or orangeade, white and red grape juices, grapefruit juice, apple juice, pear juice, cranberry juice, blueberry juice, raspberry juice, cherry juice, pineapple juice, pomegranate juice, mango juice, apricot juice or nectar, strawberry juice, kiwi juice) and vegetable juices (including but not limited to tomato juice, carrot juice, celery juice, beet juice, parsley juice, spinach juice, and lettuce juice). The juices may be in any form, including liquid, solid, or semi-solid forms such as gels or other concentrates, ices or sorbets, or powders, and may also contain suspended solids.

In another embodiment, fruit-flavored or other sweetened substances, including naturally flavored, artificially flavored, or those with other natural flavors ("WONF"), may be used instead of fruit juice. Such fruit flavored substances may also be in the form of liquids, solids, or semi-solids, such as powders, gels or other concentrates, ices, or sorbets, and may also contain suspended solids.

Proteins suitable for the edible food products incorporating the stabilizer compositions include food proteins and amino acids, which can be beneficial to mammals, birds, reptiles, and fish. Food proteins include animal or plant proteins and fractions or derivatives thereof. Animal derived proteins include milk and milk derived products, such as heavy cream, light cream, whole milk, low fat milk, skim milk, fortified milk including protein fortified milk, processed milk and milk products including superheated and/or condensed, sweetened or unsweetened skin milk or whole milk, dried milk powders including whole milk powder and nonfat dry milk (NFDM), casein and caseinates, whey and whey derived products such as whey concentrate, delactosed whey, demineralized whey, whey protein isolate. Egg and egg-derived proteins may also be used. Plant derived proteins include nut and nut derived proteins, sorghum, legume and legume derived proteins such as soy and soy derived products such as untreated fresh soy, fluid soy, soy concentrate, soy isolate, soy flour, and rice proteins, and all forms and fractions thereof. Food proteins may be used in any available form, including liquid, condensed, or powdered. When using a powdered protein source, however, it may be desirable to prehydrate the protein source prior to blending with stabilizer compositions and juice for added stability of the resulting beverage. When protein is added in conjunction with a fruit or vegetable juice, the amount used will depend upon the desired end result. Typical amounts of protein range from about 1 to about 20 grams per 8 oz. serving of the resulting stable edible food products, such as beverages, but may be higher depending upon the application.

Other products and applications for which the present compositions, or stabilizer compositions, may be used include industrial suspensions. In some embodiments, the industrial suspensions include the present compositions that are adapted for use in pharmaceuticals, cosmetics, personal care products, agricultural products, or chemical formulations. Some examples of applications include use as an excipient for oral dose forms such as tablets and chewable tablets, taste masking for drug actives (such as APAP, aspirin, ibuprofen, etc.); suspending agent; controlled release agent in pharmaceutical applications; delivery system for flavoring agents and nutraceutical ingredients in food, pharmaceutical, and agricultural applications; direct compression sustained release agent, which can be used in pharmaceutical dosage forms such as tablets, films, and suspensions; thickener, which can be used in foams, creams, and lotions for personal care applications; suspending agent, which can be used with pigments and fillers in ceramics, colorants, cosmetics, and oral care; material in ceramics; delivery system for pesticides including insecticides and other agricultural products.

The three-component co-attrited compositions of the present invention are dry blended with the additional ingredients. At least one of an additional hydrocolloid, a surfactant, an active substance, and/or a filler can be dry blended with the co-attrited stabilizer composition. Such blends are suitable intermediates that can be dosed and dispersed with sufficient water and agitation with heat as appropriate to activate the stabilizer in the desired food, pharmaceutical, industrial, or cosmetic product or application.

In alternative embodiments, at least one of an additional hydrocolloid, a surfactant, an active substance, and/or a filler may be added to a slurry of the three component co-attrited composition, and the slurry is then spray dried.

Suitable additional hydrocolloids that may be added to a dry blend or slurry containing the co-attrited composition can be any used in the food industry. These hydrocolloids include, but are not limited to, starches and modified starches, water-soluble and water-dispersible gums, polysaccharides, and synthetic polymers, such as, for example, pectins, including high methoxyl ("HM") and low methoxyl pectins and acetylated pectins (such as beet pectin), carboxymethyl cellulose, high degree-of-substitution ("high DS") carboxymethyl cellulose, alginate, carrageenans (iota, lambda, kappa), karaya gum, xanthan gum, arabic gum, gellan gum, PGA, PES carrageenan, tragacanth, and galactomannans (such as guar gum, locust bean gum, tara gum, cassia gum), Konjac gums, tamarind seed gum, and mixtures thereof. In some embodiments, the additional hydrocolloid is starch, xanthan gum, high DS carboxymethyl cellulose, pectin, sodium iota carrageenan, sodium alginate. In alternative embodiments, additional hydrocolloid is added in a supplementary step in an amount suited to the particular end product being manufactured. These additional hydrocolloids are employed in amounts sufficient to enhance the stabilizing function of the three-component compositions in the final food, pharmaceutical, industrial, or cosmetic product. For example, in a beverage, an adjunct stabilizer can be employed in a sufficient amount to further reduce serum separation in the final beverage.

Suitable surfactants include, but are not limited to, ionic or nonionic with an HLB of 1 to 40. Active substances may be added to the compositions and include, but are not limited to, at least one of a nutraceutical agent, a vitamin, a mineral, a coloring agent, a sweetener, a flavorant, a fragrance, a salivary stimulant agent, a food, an oral care agent, a breath freshening agent, a pharmaceutical active, agricultural active, therapeutic agent, cosmetic agent, chemical, buffer, or pH modifier. Active substances can be encapsulated or otherwise processed or treated to modify their release properties.

The particular filler used depends upon its ability to modify the blend and/or the desired product. Insoluble fillers, such as pigments like titanium dioxide, and insoluble but swellable fillers, such as gel particles, celluloses or microcrystalline cellulose, form suspensions or dispersions with the activated stabilizer. Alternatively, fillers can be water-soluble and capable of readily dissolving in water (such as sugar or maltodextrin) or reactive (for example, pH-sensitive or temperature-sensitive) and capable of dissolving under specific process conditions (such as calcium carbonate).

When manufacturing edible products or beverages having a low-pH phase and a protein phase it is also possible to achieve a desirable level of stability by manufacturing edible products or beverages in a single phase. In such a single-phase process, the stabilizer composition and optional additional hydrocolloid may be dispersed in water. Additional ingredients, including but not limited to proteins, fruit juices, acidulants, buffers, sweeteners, pH modifiers, anti-foaming agents, and salts may then be added to the present compositions in a single phase. The order of addition of any additional ingredients should be selected to insure protein protection both during assembly of the edible product or beverage and thereafter.

Other ingredients may also be added to the edible compositions, or edible food products, disclosed herein. Such additional ingredients which may be desirable and can include, but are not limited to, pH modifiers such as acidulants (including citric, malic, tartaric, phosphoric, acetic, and lactic acids and the like), buffering agents (including carbonates, citrates, phosphates, sulfates, maleates, and the like), or the like that may be added to either the juice or protein components at any stage of production, sweeteners (such as sugar, corn syrup, fructose, etc.), high intensity sweeteners (such as aspartame), sweetener alternatives (such as sucralose) or sugar alcohols (such as sorbitol, mannitol, and maltitol). In one embodiment, a sugar alternative such as sucralose, aspartame, or acesulfame K is used to produce a resulting composition that is low in carbohydrate content. Further possible additives include flavors, colorants, emulsifiers, preservatives, fillers such as maltodextrins, alcohol compositions, concentrates, and nutritional additives (such as calcium, i.e., calcium maleate or other minerals, vitamins, herbal supplements, etc.). Optional process aids such as an antifoam agent may also be used in these applications.

Edible food products that can benefit from the stabilizer compositions of the present invention include low pH liquids, wherein the resulting pH is greater than about 2.5 and less than about 7.0. In one embodiment, the pH of the food product is between about 2.8 and about 6.5. In a further embodiment, the pH of the food product is between about 3.0 and about 6.0. The pH can also be less than about 5.5. The compositions can be either alcoholic or non-alcoholic in nature.

The final beverage compositions may be processed by heat treatment in any number of ways. These methods may include, but are not limited to, pasteurization, ultra pasteurization, high temperature short time pasteurization ("HTST"), and ultra high temperature pasteurization. These beverage compositions may also be retort processed, either by rotary retort or static retort processing. Some compositions, such as juice-added or natural or artificially flavored soft drinks may also be cold processed. Many of these processes may also incorporate homogenization or other shearing methods. There may also be co-dried compositions, which can be prepared in dry-mix form, and then conveniently reconstituted for consumption as needed. The resulting beverage compositions may be refrigerated and stored for a commercially acceptable period of time. In the alternative, the resulting beverages may be stored at room temperature, provided they are filled under aseptic conditions.

The disclosed edible food products have enhanced storage stability and, therefore, greater commercial appeal. Stable compositions are those that exhibit acceptable levels of storage stability. Storage stability is intended to mean at least one or more of the following product characteristics over the desired shelf life of the product: in liquid systems, suspensions with minimal or no sedimentation, minimal or no serum separation, minimal or no creaming, minimal or no mottling, absence of rippling, absence of localized gels or gelation; in solid, semi-solid, gel, foam or film systems, minimal or no serum separation, deaeration or coalescence; and additionally for frozen systems, reduction or avoidance of the growth in size or number of ice crystals.

It will be recognized that the weight percents of the ingredients in the stabilizer composition of the invention in food and beverage products may be adjusted accordingly to attain the desired results, such as protein stability. Such routine adjustment of the composition is fully within the capabilities of one having skill in the art and is within the scope and intent of the present invention.

In order to describe the invention in more detail, the following non-limiting examples are provided. Unless otherwise indicated herein, all parts, percents, ratios and the like are by weight.

EXAMPLES

In the following examples, except as otherwise noted, the suspension/dispersions were made using a Waring blender whereby the powdered composition was added to water under low shear and then mixed for two minutes under high shear. After two minutes of high shear mixing, the mixing was stopped and the suspensions rested for 30 seconds prior to commencing the analyses set forth herein. All gel strengths (G') were measured using a TA-Instruments rheometer (ARES-RFS3) with oscillatory strain sweep at 1 Hz and at 20° C., with gap size at 1.8 mm in a 2.6% solids water (de-ionized) dispersion after 24 hours, and all viscosities of the co-attrited compositions are Brookfield viscosities measured to determine their initial and set up viscosity (after 24 hours) in a 2.6% solids dispersion in de-ionized water using a Brookfield RVT viscometer, with an appropriate spindle, at 20 rpm and 20° to 23° C.

Example 1: Three Component Co-Extrusion of MCC:High DS CMC:Starch

Case A:

MCC wet cake (43% solids) was co-extruded with 12M8F carboxymethyl cellulose (DS of about 1.2) and tapioca starch (National Frigex HV, National Chemical Company, Bridgewater, N.J.) at a weight ratio of 65.4:11.5:23.1. No salt solution was used as an attriting aid. The extrusion generated a very good work profile and the extrudate was not slippery. The extrudate was then redispersed in de-ionized water, homogenized, and spray-dried into powder. Activation of this powder at 2.6% solids in de-ionized water demonstrated a Brookfield initial viscosity of 2,950 cps and a Brookfield set-up (24 hrs) viscosity of 3,000 cps. The 2.6% solids dispersion was measured after 24 hrs set-up by a Texas Instruments Rheometer and exhibited a gel strength (G') of 50 Pa. The colloidal content was 66.1%.

Case B:

MCC wet cake (43% solids) was co-extruded with 12M31P carboxymethyl cellulose (DS of about 1.2) and tapioca starch (National Frigex HV) at a weight ratio of 65.4:11.5:23.1. No salt solution was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 3,500 cps and a Brookfield set-up (24 hrs) viscosity of 3,700 cps. The colloidal content was 67.4%.

Case C:

MCC wet cake (~40% solids) was co-extruded with 12M31P carboxymethyl cellulose and tapioca starch (National Frigex HV) at a weight ratio of 60.7:10.7:28.6. No salt solution was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 4,200 cps and a Brookfield set-up (24 hrs) viscosity of 4,200 cps. The 2.6% solids dispersion was measured after 24 hrs set-up by a Texas Instruments Rheometer and exhibited a gel strength (G') of 68 Pa. The colloidal content was 77%.

Case D:

MCC wet cake (~43% solids) was extruded with 12M31P carboxymethyl cellulose and tapioca starch (National Frigex HV) at a weight ratio of 60.7:10.7:28.6. No salt solution was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 4,000 cps and a Brookfield set-up (24 hrs)

viscosity of 4,150 cps. The 2.6% solids dispersion was measured after 24 hrs set-up by a Texas Instruments Rheometer and exhibited a gel strength (G') of 60 Pa. The colloidal content was 81%.

Example 2 (Comparative): Three-Component Co-Extrusion of MCC:CMC Having DS of 0.7:Starch MCC wet cake (at 40% solid) was blended in a Hobart mixer with 7LF carboxymethyl cellulose (Ashland; DS of 0.74-0.85) and tapioca starch (National Frigex HV, National Starch and Chemical Company, Bridgewater, N.J., USA) at the weight ratio of 61.5:15.4:23.1. No salt solution was used as an attriting aid. The admixture was then extruded, redispersed in water, homogenized, and spray-dried into powder. Activation of this powder at 2.6% solids demonstrated a Brookfield initial viscosity of 950 cps and a Brookfield set-up (24 hr) viscosity of 4,000 cps. The 2.6% solids dispersion was measured after 24 hrs set-up by a Texas Instruments Rheometer and exhibited a gel strength (G') of 20 Pa. The colloidal content was 87.7%.

Example 3 (Comparative): Two-Component Co-Extrusion of MCC:CMC

MCC wet cake was extruded with 12M31P carboxymethyl cellulose (Ashland) at a 85:15 weight ratio. No salt solution was used as an attriting aid. The extrudate was slippery, generated a very low work profile in extrusion, and yielded inferior colloidal product. Activation of this powder at 2.6% solids demonstrated a Brookfield initial viscosity of 780 cps and a Brookfield set-up (24 hr) viscosity of 1,120 cps. The 2.6% solids dispersion was measured after 24 hrs set-up by a Texas Instruments Rheometer and exhibited a gel strength (G') of about 9 Pa.

Example 4 (Comparative): Two-Component Co-Extrusion of MCC:Ambergum 1221 CMC Direct extrusion of MCC wet cake with Ambergum 1221 (carboxymethyl cellulose having a DS of 1.2 and low viscosity (Ashland)) at a 85:15 weight ratio produced a very low work profile in extrusion. No salt solution was used as an attriting aid. The extrudate looked "wet" and dense. The extrudate was redispersed in water, homogenized, and spray-dried into powder. Activation of the powder at 2.6% solids in de-ionized water demonstrated a very weak gel structure. The Brookfield initial viscosity was 275 cps and a Brookfield set-up (24 hrs) viscosity was 660 cps. The material had a relatively low colloidal content of 59% and a gel strength (G') of 15 Pa. The gel strength of this sample was not as high as the gel strengths of the present invention. As a result, this sample would not be as ideal as the present invention in those situations where a higher gel strength is desired.

Example 5: Three-Component Co-Extrusion of MCC:Pectin:Starch

MCC wet cake (~40% solids) was co-extruded with Grinsted® AMD-78351 pectin (Danisco A/S, Copenhagen, Denmark) and National Frigex HV tapioca starch at a weight ratio of 65.4:11.5:23.1. No salt solution was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 840 cps and a Brookfield set-up (24 hrs) viscosity of 880 cps. The 2.6% solids dispersion was measured after 24 hrs set-up by a Texas Instruments Rheometer and exhibited a gel strength (G') of about 60 Pa. In comparison, a commercial material (see Example 13) made from MCC/pectin/salt extrusion had a gel strength (G') of 6-14 Pa.

Example 6: Three-Component Co-Extrusion of MCC:Pectin:Starch

MCC wet cake (~40% solids) was co-extruded with Grinsted® AMD-78351 pectin (Danisco A/S) and National Frigex HV tapioca starch, at a weight ratio of 57.1:14.3:28.6. No salt solution was used as an attriting aid. The extrusion generated very good work profile and the extrudate was not slippery. The extrudate was then redispersed in de-ionized water, homogenized, and spray-dried into powder. Activation of this powder at 2.6% solids in de-ionized water demonstrated a Brookfield initial viscosity of 840 cps and a Brookfield set-up (24 hrs) viscosity of 900 cps. The 2.6% solids dispersion was measured after 24 hrs set-up by a Texas Instruments Rheometer and exhibited a gel strength (G') of about 50 Pa. In comparison, a commercial material (see Example 13) made from MCC/pectin/salt extrusion had a gel strength (G') of 6-14 Pa.

Example 7: Three-Component Co-Extrusion of MCC:Alginate:Starch

MCC wet cake (~40% solids) was co-extruded with sodium alginate (Kelset) from FMC, and National Frigex HV tapioca starch, at a weight ratio of 57.1:14.3:28.6. No salt was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 2,200 cps and a Brookfield set-up (24 hrs) viscosity of 2,600 cps. The 2.6% solids dispersion was measured after 24 hrs set-up by a Texas Instruments Rheometer and exhibited a gel strength (G') of about 90 Pa.

Example 8: Three-Component Co-Extrusion of MCC:Extract Carregeenan:Starch

MCC wet cake (~40% solids) was co-extruded with Lactarin MV306 carrageenan (lambda-type based) from FMC, and National Frigex HV tapioca starch, at a weight ratio of 57.1:14.3:28.6. No salt was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 1,000 cps and a Brookfield set-up (24 hrs) viscosity of 700 cps. The 2.6% solids dispersion was measured after 24 hrs set-up by a Texas Instruments Rheometer and exhibited a gel strength (G') of about 60 Pa.

Example 9: Three-Component Co-Extrusion of MCC:Semi-Refined Carrageenan:Starch MCC wet cake (~40% solids) was co-extruded with semi-refined kappa-type carrageenan from FMC and National Frigex HV Tapioca starch at a weight ratio of 65.4:11.5:23.1. No salt was used as an attriting aid. The extrusion generated very good work profile and the extrudate was not slippery. The extrudate was then redispersed in de-ionized water, homogenized and spray-dried into powder. Activation of this powder at 2.6% solids in de-ionized water demonstrated a Brookfield initial viscosity of 700 cps, a set-up viscosity of 1,500 cps and a gel strength (G') of about 85 Pa.

Example 10: Dry Blending of Guar Gum with Three-Component Product MCC:PES Carrageenan:Starch Guar gum (DP 130) was dry blended with the three-component attrited product (MCC:carrageenan:starch) of Example 9 at a wt % ratio of 25:75. Activation of this combined powder at 2.6% solids in de-ionized water demonstrated a Brookfield initial viscosity of 3,000 cps and a Brookfield set-up (24 hrs) viscosity of 4,500 cps. The 2.6% solids dispersion was measured after 24 hrs set-up by a Texas Instruments Rheometer and exhibited a gel strength (G') of about 45 Pa.

Example 11 (Comparative)

A commercially available colloidal MCC made with a low viscosity carboxymethyl cellulose having a DS of 0.7±0.15 was tested. When dispersed in de-ionized water at room temperature, at 2.6% solids, it exhibited an initial Brookfield viscosity of 50-151 cps and a set-up viscosity after 24 hrs of 2,500 cps. When the 2.6% solids dispersion was measured by a Texas Instruments Rheometer after 24 hrs set-up, it exhibited a gel strength (G') of 9 Pa. A colloidal content of 77% was obtained, which was determined by centrifugation of the water dispersion at 8,250 rpm for 15 minutes followed by gravimetric analysis of the dried supernatant portion.

Example 12 (Comparative)

Another commercially available colloidal MCC was made with a carboxymethyl cellulose having a DS of 1.2 and medium viscosity. An attriting salt solution was used in its manufacture. When dispersed in de-ionized water at room temperature at 2.6% solids, it exhibited an initial Brookfield viscosity of 1,650 cps, and a set-up viscosity after 24 hrs of 3,250 cps. When the 2.6% solids dispersion was measured by a Texas Instruments Rheometer after 24 hrs set-up, it exhibited a gel strength (G') of 15 Pa. A colloidal content of 80% was obtained, which was determined by centrifugation of the water dispersion at 8,250 rpm for 15 minutes followed by gravimetric analysis of the dried supernatant portion.

Example 13 (Comparative)

A commercially available colloidal MCC stabilizer containing pectin and calcium chloride was tested. When this was dispersed in de-ionized water at room temperature at 2.6% solids, it exhibited an initial Brookfield viscosity of 600-1,200 cps and a set-up viscosity after 24 hrs of 1,400-2,200 cps. When the 2.6% solids dispersion was measured by a Texas Instruments Rheometer after 24 hrs set-up, it exhibited a gel strength (G') of 6-14 Pa.

Example 14: UHT Chocolate Beverages

Materials and Methods:

Samples of UHT chocolate beverages were prepared using: A) a mixture of 0.15% of the MCC product from Example 11 and 0.01% carrageenan (comparative sample; "Sample A"); and B) a combination of 0.15% MCC/CMC/starch as made by Example 1, Case D, and 0.01% carrageenan (inventive sample; "Sample B").

Process:

All powders were dry blended together and mixed for approximately 15 minutes in the cold pasteurized milk using a high shear mixer. The milk product was first preheated at 75° C. for 45 seconds and then sterilized at 142° C. for 5 seconds using a UHT (ultra high temperature) process. The product was then cooled to 70-80° C. and passed through a Rannie homogenizer with a two-stage pressure of 180 bars. Finally, the mixture was cooled to 10° C. and aseptically filled in sterile bottles. Stability index of the resulting materials was measured using a Turbiscan equipment. A lower stability index number indicates better stability (e.g., a more uniform disperson/suspension over time with less settling). The product was scanned with a beam of light at 880 nm near infrared; backscattering or transmission was recorded at small intervals (one scan every 40 μm) across the length of the sample. Changes in backscattering indicated changes in particle size or the aggregation of particles.

Visual parameters and the scale used for evaluation are described in Table 1.

TABLE 1

| Visual Parameters | Explanation | Standard Scale to be used |
|---|---|---|
| On the 250 ml bottle after preparation, but before any further manipulation | | |
| Creaming | Fat separation at the top | 0 = absence; 1 = 0.5 mm; 2 = 0.5 to 1 mm; 3 = 1 to 2 mm; 4 > 2 mm. |
| Clear Top Separation | Visual Transparent Layer at the Top | 0 = absence; 1 = >0-2 mm; 2 = >2-4 mm; 3 = >4-6 mm; 4 = >6 mm. |
| Marbling | Clear Layers of Whey Inside the Product (waves) | 0 = absence; 1 = very slight marbling; 2 = slight marbling; 3 = strong marbling (not acceptable); 4 = very strong marbling (not acceptable). |
| Sedimentation Layer | Cocoa or Particles Layer at the Bottom of the Liquid | 0 = absence; 1 = 0.5 mm; 2 = 0.5 to 1 mm; 3 = 1 to 2 mm; 4 > 2 mm. |
| In a 250 ml glass beaker or cylinder during and after pouring | | |
| Flow Properties | During pouring evaluate level of ripple until gelled pieces are visible. | 0 = absence of ripple; 1 = slight ripple; 2 = ripple; 3 = strong ripple, makes noise while pouring (not acceptable); 4 = gelled pieces (not acceptable). |

TABLE 1-continued

| Visual Parameters | Explanation | Standard Scale to be used |
| --- | --- | --- |
| Sedimentation at the bottom | After pouring, proteins or particles (e.g., cocoa, calcium) are visible at the bottom of the bottle. | 0 = absence of sedimentation; 1 = very slight sedimentation; 2 = slight sedimentation; 3 = strong sedimentation (not acceptable); 4 = very strong sedimentation (not acceptable). |
| Re-dispersibility | Evaluation of the possibility to re-disperse the sedimentation of proteins or particles (e.g., calcium, cocoa, etc.) when the product is poured multiple times. | 0 = absence of sedimentation; 1 = sedimentation disappears after 1 time redispersing (=2 times poured); 2 = sedimentation disappears after 2 times redispersing; 3 = sedimentation disappears after 3 times redispersing; 4 = sedimentation disappears after 4 times redispersing. |

Evaluation of the Samples:

Results of pH, viscosity, and visual observation after one month storage at 4° C., 22° C., and 30° C. are described in the tables below. The pH was measured using a calibrated pH meter (Inolab). Viscosity was measured using a Brookfield viscometer with spindle LV 61 at speed 60 rpm for one minute. Turbiscan measurements were made at 30° C. for 5 days, which is also displayed. The % set forth in the following tables is all weight percent.

TABLE 2

| 0.15% Dosage (4° C., 1 month) | 0.15% Sample A (comparative) % | 0.15% Sample B (invention) % |
| --- | --- | --- |
| Ingredients + SKU | | |
| Semi-skim milk (1.5% fat) | Make up to 100 | Make up to 100 |
| Sugar | 7.5 | 7.5 |
| Cocoa powder D-11 A | 1.5 | 1.5 |
| Carrageenan | 0.01 | 0.01 |
| Stabilizer | 0.15 | 0.15 |
| TOTAL | 100 | 100 |
| Results at 1 month | | |
| pH | 6.839 | 6.884 |
| Viscosity | 39.5 | 41.5 |
| Visuals parameters on 250 ml bottle before any manipulation | | |
| Creaming | 1 | 1 |
| Top Clear separation | 0 | 0 |
| Marbling | 1 | 0 |
| Sedimentation layer | 1 | 0 |
| In a glass beaker or Brookfield cylinder during and after pouring | | |
| Flow properties | 0 | 2 |
| Flocculation | 0 | 0 |
| Sedimentation at the bottom | 1 | 0 |
| Redispersibility | 2 | 0 |

TABLE 3

| 0.15% Dosage (22° C., 1 month) | 0.15% Sample A (comparative) % | 0.15% Sample B (invention) % |
| --- | --- | --- |
| Ingredients + SKU | | |
| Semi-skim milk (1.5% fat) | Make up to 100 | Make up to 100 |
| Sugar | 7.5 | 7.5 |
| Cocoa powder D-11 A | 1.5 | 1.5 |
| Carrageenan | 0.01 | 0.01 |
| Stabilizer | 0.15 | 0.15 |
| TOTAL | 100 | 100 |
| Results at 1 month | | |
| pH | 6.691 | 6.735 |
| Viscosity | 17.7 | 24.0 |
| Visuals parameters on 250 ml bottle before any manipulation | | |
| Creaming | 0 | 1 |
| Top Clear separation | 2 | 0 |
| Marbling | 2 | 1 |
| Sedimentation layer | 2 | 0 |
| In a glass beaker or Brookfield cylinder during and after pouring | | |
| Flow properties | 2 | 1 |
| Flocculation | 0 | 0 |
| Sedimentation at the bottom | 1 | 0 |
| Redispersibility | 1 | 0 |

TABLE 4

| 0.15% Dosage (30° C., 1 month) | 0.15% Sample A (comparative) % | 0.15% Sample B (inventive) % |
| --- | --- | --- |
| Ingredients + SKU | | |
| Semi-skim milk (1.5% fat) | Make up to 100 | Make up to 100 |
| Sugar | 7.5 | 7.5 |
| Cocoa powder D-11 A | 1.5 | 1.5 |
| Carrageenan | 0.01 | 0.01 |
| Stabilizer | 0.15 | 0.15 |
| TOTAL | 100 | 100 |
| Results at 1 month | | |
| pH | 6.66 | 6.691 |
| Viscosity | 12.3 | 17.8 |
| Visuals parameters on 250 ml bottle before any manipulation | | |
| Creaming | 1 | 1 |
| Top Clear separation | 0 | 0 |

TABLE 4-continued

| 0.15% Dosage (30° C., 1 month) | 0.15% Sample A (comparative) % | 0.15% Sample B (inventive) % |
|---|---|---|
| Marbling | 3 | 1 |
| Sedimentation layer In a glass beaker or Brookfield cylinder during and after pouring | 2 | 0 |
| Flow properties | 2 | 0 |
| Flocculation | 0 | 0 |
| Sedimentation at the bottom | 1 | 0 |
| Redispersibility | 1 | 0 |
| STABILITY INDEX | | |
| Bottom | 6.18 | 0.86 |
| Global | 2.83 | 0.76 |
| Top | 3.53 | 3.29 |

Conclusion:

Visually, Sample B (present invention) was stable for one month at 4° C., 22° C., and 30° C. with no or trace serum separation, no or trace cocoa sedimentation, and with no or minimal gelation. Low stability indexes (i.e., better suspension stability) of Sample B compared to Sample A confirmed the visual observations and visual stability. In distinction, Sample A demonstrated less stability and inferior performance relative to Sample B.

Example 15

MCC wet cake (41.6%) was co-extruded with sodium alginate (Kelset) from FMC and Novation 3300 (tapioca starch) at a weight % ratio of 50:25:25, respectively. No salt was used as an attriting aid. The extrusion generated very good work profile and the extrudate was not slippery. The extrudate was then redispersed in deionized water and spray dried into powder. Activation of this powder at 2.6% solids in de-ionized water demonstrated a Brookfield initial viscosity of 1,800 cps and a set-up (24 hrs) viscosity of 9,600 cps. The 2.6% solids dispersion measured after 24 hrs set-up by a Texas Instruments Rheometer exhibited a gel strength (G') of about 42 Pa.

While the invention has been described in detail and with reference to specific embodiments thereof, it will be apparent to one skilled in the art that various changes and modifications can be made therein without departing from the spirit and scope thereof.

What is claimed is:

1. A co-attrited stabilizer composition comprising:
   a) microcrystalline cellulose in an amount of from 20%-90% by weight of the composition;
   b) a hydrocolloid in an amount of from 5%-50% by weight of the composition, wherein the hydrocolloid is selected from at least one member of the group consisting of carboxymethyl cellulose having a degree of substitution of from 0.95 to 1.5, pectin, alginate, carrageenan, xanthan gum, agar gum, wellan gum, or gelian gum; and
   c) a starch in an amount of from 5%-50% by weight of the composition;
   wherein the stabilizer composition has a gel strength (G') of at least 25 Pa when measurement is made using a TA-Instruments rheometer (ARES-RFS3) with oscillatory strain sweep at 1 Hz and at 20° C., with gap size at 1.8 mm measured after 24 hours in a 2.6% solids in de-ionized water dispersion at 20° C.

2. The stabilizer of claim 1, wherein said gel strength (G') is at least 42 Pa.

3. The stabilizer composition of claim 1, wherein said hydrocolloid is present in an amount of from 5%-30% and said gel strength (G') is at least 50 Pa.

4. The stabilizer composition of claim 1, wherein the microcrystalline cellulose is present in an amount of from 45 to 70% by weight of the composition, the hydrocolloid is present in an amount of from 10-30% by weight of the composition, and the starch is present in an amount of from 20-50% by weight of the composition.

5. The stabilizer composition of claim 1, wherein the hydrocolloid is carboxymethyl cellulose present in an amount of 5% to 20% by weight of the composition.

6. The stabilizer composition of claim 1, wherein the carboxymethyl cellulose is present in an amount of from 5%-30%.

7. The stabilizer composition of claim 1, wherein the carboxymethyl cellulose has a degree of substitution of from 1.15 to 1.5 and is present in an amount of from 5%-30%.

8. The stabilizer composition of claim 1, wherein the hydrocolloid is at least one carrageenan comprising kappa carrageenan, kappa-2 carrageenan, iota carrageenan, or lambda carrageenan, and mixtures thereof.

9. The stabilizer composition of claim 1, wherein the starch is selected from at least one member of the group consisting of wheat, corn, oat, rice, tapioca, or potato.

10. The stabilizer composition of claim 1, wherein the starch comprises a tapioca starch.

11. The stabilizer composition of claim 1, wherein said composition does not contain a co-attriting agent.

12. A method for making the stabilizer composition of claim 1 comprising:
   a) admixing the microcrystalline cellulose, hydrocolloid, and starch;
   b) co-attriting the admixture of step a) to obtain an extrudent; and
   c) drying the extrudent of step b).

13. The method of claim 12, wherein the drying of step c) is spray drying.

14. The method of claim 12, wherein said co-attriting is co-extruding.

15. The method of claim 12, wherein step b) is performed without the use of a co-attriting salt.

16. A food comprising the stabilizer composition of claim 1.

17. The food of claim 16, wherein the food is a beverage.

18. The food of claim 17, wherein the beverage has a pH of from 2-7.

19. The food of claim 17, wherein the beverage comprises milk.

20. The food of claim 12, wherein the stabilizer composition is present in an amount of from 0.05 to 3.5% by total weight of the food.

21. A suspension comprising the stabilizer composition of claim 1 suitable for use in pharmaceutical products, nutraceutical products, cosmetic products, personal care products, or agricultural products.

22. A stabilizer composition of claim 1 prepared by a process comprising the steps:
   a) admixing the microcrystalline cellulose, hydrocolloid, and starch;
   b) co-attriting the admixture of step a) to obtain an extrudent; and
   c) drying the extrudent of step b).

* * * * *